(12) United States Patent
Lehr et al.

(10) Patent No.: US 12,198,530 B2
(45) Date of Patent: Jan. 14, 2025

(54) CONTINGENT AID DEVICE, SYSTEM, AND METHOD FOR COMMUNICATING WITH AN EMERGENCY CONTACT

(71) Applicant: LETSUNDOIT, LLC, King of Prussia, PA (US)

(72) Inventors: Audrey M. Lehr, Wyomissing, PA (US); Mark Eike, Clermont, FL (US); Kenneth Maurice Jackson, Colorado Springs, CO (US); Baiju Paul Mathews, Cupertino, CA (US)

(73) Assignee: LETSUNDOIT, LLC, King of Prussia, PA (US)

( * ) Notice: Subject to any disclaimer, the term of this patent is extended or adjusted under 35 U.S.C. 154(b) by 466 days.

(21) Appl. No.: 17/595,899

(22) PCT Filed: Jul. 6, 2021

(86) PCT No.: PCT/US2021/040455
§ 371 (c)(1),
(2) Date: Nov. 29, 2021

(87) PCT Pub. No.: WO2022/010856
PCT Pub. Date: Jan. 13, 2022

(65) Prior Publication Data
US 2022/0223027 A1 Jul. 14, 2022

Related U.S. Application Data

(60) Provisional application No. 63/049,333, filed on Jul. 8, 2020, provisional application No. 63/158,452, filed on Mar. 9, 2021.

(51) Int. Cl.
*G08B 25/01* (2006.01)
*A61J 1/03* (2023.01)
(Continued)

(52) U.S. Cl.
CPC .............. *G08B 25/016* (2013.01); *A61J 1/03* (2013.01); *G16H 20/13* (2018.01); *G16H 40/63* (2018.01)

(58) Field of Classification Search
CPC .................................. A61J 1/03; G08B 25/016
(Continued)

(56) References Cited

U.S. PATENT DOCUMENTS 7,261,691 B1 8/2007 Asomani
8,275,352 B2 9/2012 Forstall et al.
(Continued)

OTHER PUBLICATIONS

PCT Notification of Transmittal of the International Search Report and the Written Opinion of the International Searching Authority, or the Declaration issued to counterpart application PCT/US21/40455 dated Oct. 20, 2021.

*Primary Examiner* — Fabricio R Murillo Garcia
(74) *Attorney, Agent, or Firm* — McNees Wallace & Nurick LLC (57) ABSTRACT

A contingent aid device, system, and method are disclosed including a cavity with lid to hold a medicine, a control module, a lid status sensor, a medicine status sensor, a user-activatable tactile input, a status indicator module, a display screen, a communication module, a global positioning system module, an altimeter, a voice-in module, an audio-out module, a digital-in module, and a power source, wherein the device is configured to, without further user-initiated instruction or action, initiate communication with an emergency contact following removal of the medicine from the cavity, following user activation of the user-activatable tactile input, following a first predetermined period of time after opening of the lid without removal of the medicine from the cavity, or following a second predetermined period of time after removal of the medicine from the (Continued)

cavity without user activation of the user-activatable tactile input confirming the medicine has been administered.

20 Claims, 10 Drawing Sheets

(51) Int. Cl.
 *G16H 20/13* (2018.01)
 *G16H 40/63* (2018.01)
(58) Field of Classification Search
 USPC ..................................................... 455/404.2
 See application file for complete search history.

(56) References Cited

U.S. PATENT DOCUMENTS

| | | | |
|---|---|---|---|
| 8,361,026 B2 | 1/2013 | Edwards et al. | |
| 8,361,029 B2 | 1/2013 | Edwards et al. | |
| 8,425,462 B2 | 4/2013 | Edwards et al. | |
| 8,441,356 B1 | 5/2013 | Tedesco et al. | |
| 8,544,645 B2 | 10/2013 | Edwards et al. | |
| 8,608,698 B2 | 12/2013 | Edwards et al. | |
| 8,622,973 B2 | 1/2014 | Edwards et al. | |
| 8,627,816 B2 | 1/2014 | Edwards et al. | |
| 8,690,827 B2 | 4/2014 | Edwards et al. | |
| 8,920,367 B2 | 12/2014 | Edwards et al. | |
| 8,926,594 B2 | 1/2015 | Edwards et al. | |
| 8,977,294 B2 | 3/2015 | De Atley | |
| 9,022,980 B2 | 5/2015 | Edwards et al. | |
| 9,084,849 B2 | 7/2015 | Edwards et al. | |
| 9,173,999 B2 | 11/2015 | Edwards et al. | |
| 9,204,796 B2 | 12/2015 | Tran | |
| 9,238,108 B2 | 1/2016 | Edwards et al. | |
| 9,327,077 B2 | 5/2016 | Edwards et al. | |
| 9,619,621 B2 | 4/2017 | Dicks et al. | |
| 9,742,709 B1 | 8/2017 | Laich | |
| 9,778,280 B2 | 10/2017 | Yuen et al. | |
| 9,841,494 B2 | 12/2017 | Meadow | |
| 9,848,058 B2 | 12/2017 | Johnson et al. | |
| 9,940,808 B2 | 4/2018 | Shapiro et al. | |
| 9,980,113 B2 | 5/2018 | Miner et al. | |
| 10,004,883 B2 | 6/2018 | Anderson | |
| 10,015,649 B2 | 7/2018 | Ulmansky et al. | |
| 2006/0207911 A1* | 9/2006 | Bullock | B65D 75/305 |
| | | | 206/530 |
| 2010/0169111 A1 | 7/2010 | Brue et al. | |
| 2013/0195326 A1* | 8/2013 | Bear | A61J 7/0084 |
| | | | 382/128 |
| 2013/0229282 A1* | 9/2013 | Brent | H04W 4/029 |
| | | | 340/540 |
| 2015/0272825 A1 | 10/2015 | Lim et al. | |
| 2016/0328952 A1 | 11/2016 | Will et al. | |
| 2017/0162033 A1* | 6/2017 | Fisher | H04W 68/02 |
| 2017/0296435 A1 | 10/2017 | Ziv et al. | |
| 2017/0325056 A1* | 11/2017 | Mehta | H04W 4/02 |
| 2019/0105235 A1 | 4/2019 | Seo et al. | |
| 2021/0177318 A1* | 6/2021 | Lintereur | G16H 40/63 |

* cited by examiner

CONTINGENT AID DEVICE, SYSTEM, AND METHOD FOR COMMUNICATING WITH AN EMERGENCY CONTACT

RELATED APPLICATIONS

This application claims the benefit of and priority to U.S. Provisional Patent Application No. 63/049,333, filed Jul. 8, 2020, entitled "Contemporary Consumer Device and Communication Ecosystem for Medical Emergencies," and U.S. Provisional Patent Application No. 63/158,452, filed Mar. 9, 2021, entitled "Emergency Communication System and Method," which are hereby incorporated by reference in their entirety.

FIELD OF THE INVENTION

This application is directed to devices and systems for use during medical emergencies. In particular, this application is directed to contingent aid devices and systems for tracking and communicating the dispensing of medication and contacting emergency services during medical emergencies.

BACKGROUND OF THE INVENTION

In the United States of America, emergency communications are typically initiated by a telephone dialing 911. 911 government run public-safety answering point ("PSAP") centers were created on the old analog communication system, which has been heavily disrupted by newer technologies in many domains. PSAPs have been slow to adopt or interface with new technologies, and thus PSAP centers are in varying stages of being able to accept different types of communication.

PSAPs are situated geographically in specific regions, and legacy dial up (landline) telephone calls made in these regions would automatically route through the local switching stations accordingly. These old, switched analog systems were based on two intrinsic assumptions: first, that an emergency would occur in or near the building from where a distress call originated, and second, a person would be able to verify a specific street address and speak about the emergency. In contrast, newer technologies rely on global positioning system ("GPS") coordinates and provide more accurate location information, and these are often not associated with a specific street address, nor is the mobile phone owner's home address necessarily relevant to the emergency location underway.

To help first responders better locate a mobile caller's emergency location, upcoming FCC regulations will require that increasing percentages of emergency calls made by mobile devices must provide not only latitude and longitude, but also, an elevation coordinate. The reason for this change is to help emergency responders know which floor to go to in a high-rise building, for instance. At present, many cell phones in use cannot yet comply with these regulations because making this product shift requires hardware, software, and other changes to the 911 ecosystem for these coordinates to be effectively communicated to 911.

As the consumer demand for increased communication capabilities has progressed to newer technologies, not all PSAPs were fortified to keep pace. Hence, there remains a gap in standardization or accommodation by many PSAPs to accept different emergency communication mediums and data. In the United States of America, there is no singular governing, public (government) centralized emergency (911) coordination entity that can ensure centralized and standard technology protocols across the national domain. While there are standards set by the National Emergency Number Association ("NENA"), and many telecommunications stakeholders acknowledge them, these have not been adopted by everyone touching or participating in the 911 ecosystem.

In the last century, as automated home and other real estate security systems came into being, there needed to be a way to communicate non-medical emergencies to police and other first responders. Intermediary monitoring call centers arose to be middle exchange agents between these systems and PSAPs. These centralized monitoring stations tend to be private, paid interface companies manned by human operators who would receive a distress signal from a customer's home security device and, in turn, relay a call to a local PSAPs identified in their database. Technology has advanced, and this monitoring paradigm may not be the best choice for mobile medical emergencies. While monitoring may make sense when there is a known static or a limited geographic area associated with a device, this is seldom the case for a globally mobile population.

In a home security monitoring paradigm, a call center traditionally intercepted disruptions from a home security persistent signal. A persistent monitoring signal has traditionally been transmitted through an additional physical phone line in a home, over which a home monitor to monitoring station would have a persistent 'ping'. When this was disrupted, for example by a broken circuit such as an open door, the break in the persistent signal would trigger an alarm to the monitoring center. In the event that a homeowner would not pick up the phone or verify there was an intrusion, fire, medical emergency, or other incident, the monitoring station would then notify a homeowner's local PSAP to dispatch police.

Many newer Bluetooth and BLE short range device emergency systems have carried forward the vestigial ideology of a persistent signal, e.g. for a home or medical device. Such devices pair with a mobile phone or other intermediary device so that communications from the short-range device emergency systems can subsequently flow over wire, cell, or satellite networks to monitoring stations. These devices are frequently tracked and often have an associated monitoring fee. Additionally, these devices introduce a potential point of failure due to a dependency on the performance of, and connection to, an underlying device (e.g., a cellular phone). In a medical emergency, an additional potential point of failure is a liability.

In summary, PSAPs across the United States of America are in various stages of interfacing with newer technologies for emergency information receipt and exchange, and many have no options other than to collaborate with privatized and paid vendors to upgrade their systems. Some PSAPs remain on the older analog structured system, and these PSAPs can accept voice only. In other words, PSAPs without adequate resources may not have converted their call centers to accept SMS text or internet protocol information, which may come as a surprise to app and device users who cannot connect and effectively transmit accurate location and associated relevant emergency information. It is precisely this variation in underlying PSAP ecosystem communication mediums that creates a disparity and unequal access to emergency services by today's newer devices and consumer-preferred technologies. Devices and systems which overcome these deficiencies would be desirable in the art.

BRIEF DESCRIPTION OF THE INVENTION

In one exemplary embodiment, a contingent aid device includes a cavity configured to hold a medicine, a lid configured to retain the medicine in the cavity when closed and render accessible the medicine when open, a control module, a lid status sensor configured to signal the control module if the lid is opened, a medicine status sensor configured to signal the control module if the medicine is removed from the cavity, a user-activatable tactile input, a status indicator module, a display screen, a communication module, a global positioning system module, an altimeter, a voice-in module, an audio-out module, a digital-in module, and a power source. The contingent aid device is configured to, without further user-initiated instruction or action, initiate communication with an emergency contact following removal of the medicine from the cavity, user activation of the user-activatable tactile input, a first predetermined period of time after opening of the lid without removal of the medicine from the cavity, or a second predetermined period of time after removal of the medicine from the cavity without user activation of the user-activatable tactile input confirming the medicine has been administered.

In another exemplary embodiment, a system for contingent aid communication includes a contingent aid device and a remote server in electronic communication with a control module through a communication module. The contingent aid device includes a cavity configured to hold a medicine, a lid configured to retain the medicine in the cavity when closed and render accessible the medicine when open, the control module, a lid status sensor configured to signal the control module if the lid is opened, a medicine status sensor configured to signal the control module if the medicine is removed from the cavity, a user-activatable tactile input, a status indicator module, a display screen, the communication module, a global positioning system module, an altimeter, a voice-in module, an audio-out module, a digital-in module, and a power source. The contingent aid device is configured to, without further user-initiated instruction or action, initiate communication with an emergency contact following removal of the medicine from the cavity, user activation of the user-activatable tactile input, a first predetermined period of time after opening of the lid without removal of the medicine from the cavity, or a second predetermined period of time after removal of the medicine from the cavity without user activation of the user-activatable tactile input confirming the medicine has been administered.

In another exemplary embodiment, a contingent aid communication method includes, upon an initial user activated trigger selected from the group consisting of removing a medicine from a contingent aid device, user activation of a user-activatable tactile input of the contingent aid device, a first predetermined period of time after opening the contingent aid device without removal of the medicine from the contingent aid device, and a second predetermined period of time after removal of the medicine from the contingent aid device without user activation of the user-activatable tactile input confirming the medicine has been administered, without further user-initiated instruction or action, the contingent aid device initiates communication with an emergency contact. Communication with the emergency contact includes directing a remote server to transmit a voice message to a nearest public safety answering point including a request for assistance, locational data of the contingent aid device with longitude, latitude, and elevation, as well as an address when available, and, optionally, information regarding an emergency for which the medicine is released, transmitting text messages to a predetermined recipient list with status updates including user actions taken or not taken with the contingent aid device following the initial user activated trigger, and, in the event that the voice message is unable to be sent by the remote server or received by the nearest PSAP, initiating communication with an emergency contact by placing a standard cellular emergency call. The contingent aid device includes a cavity configured to hold the medicine, a lid configured to retain the medicine in the cavity when closed and render accessible the medicine when open, a control module, a lid status sensor configured to signal the control module if the lid is opened, a medicine status sensor configured to signal the control module if the medicine is removed from the cavity, a user-activatable tactile input, a status indicator module, a display screen, a communication module, a global positioning system module, an altimeter, a voice-in module, an audio-out module, a digital-in module, and a power source.

BRIEF DESCRIPTION OF THE DRAWINGS

FIGS. 10(*a*) and 10(*b*) disclose exemplary contingent aid device status messages for display by a contingent aid device, according to an embodiment of the disclosure.

Wherever possible, the same reference numbers will be used throughout the drawings to represent the same parts.

DETAILED DESCRIPTION OF THE INVENTION

Disclosed herein are contingent aid devices, systems, and methods, which, in comparison to devices, systems, and methods not including one or more of the features described herein, decrease emergency medical response time, improve patient outcome, increase communication with emergency contacts, improve dialogue between compromised users, family, friends, and public-safety answering points or other emergency response services, or combinations thereof.

Referring to FIGS. 1-5, in one embodiment, a contingent aid device 100 includes a cavity 102 configured to hold a medicine 10, a lid 104 configured to retain the medicine 10 in the cavity 102 when closed and render accessible the medicine 10 when open, a control module 106, a lid status sensor 108 configured to signal the control module 106 if the lid 104 is opened, a medicine status sensor 110 configured to signal the control module 106 if the medicine 10 is removed from the cavity 102, a user-activatable tactile input 112, a status indicator module 114, a display screen 116, a communication module 118, a global positioning system (GPS) module 120, an altimeter 122, a voice-in module 124, an audio-out module 126, a digital-in module 128, and a power source 130. The contingent aid device 100 is configured to, without further user-initiated instruction or action, initiate communication with an emergency contact following removal of the medicine 10 from the cavity 102, user activation of the user-activatable tactile input 112, a first predetermined period of time after opening of the lid 104 without removal of the medicine 10 from the cavity 102, or a second predetermined period of time after removal of the medicine 10 from the cavity 102 without user activation of the user-activatable tactile input 112 confirming the medicine 10 has been administered. The control module 106 may be in electronic communication with a remote server 134 through the communication module 118.

The initiation of communication with the emergency contact by the contingent aid device 100 may be temporarily disabled by a user for maintenance or replacement of a medicine container 12 holding the medicine 10. Disabling initiation of communication with the emergency contact may be triggered via a user-activatable tactile input 112 or by disconnecting the power source 130. In one embodiment, each time a medicine container 12 holding the medicine 10 is loaded into the contingent aid device 100, the identity of the medicine 10 is encoded into at least one of the control module 106 or the remote server 134 such that the control module 106 or the remote server 134 may report the identity of the medicine 10 to the emergency contact when communication is initiated.

The cavity 102 may have dimensions conforming to a standard medicine 10 container 12 shape, with acceptable tolerances, or may have a replaceable inserted disposed therein which conforms to a standard medicine 10 container 12 shape, with acceptable tolerances. The cavity 102 or an insert disposed in the cavity 102 may include a shock-absorbing surface for reducing or eliminating transferal of a mechanical force applied to the contingent aid device 100 to the medicine 10.

The contingent aid device 100 may include a temperature sensor such as, but not limited to, a thermocouple, configured to monitor the temperature within the cavity 102. The cavity 102 may include a thermal element for increasing, decreasing, or maintain a predetermined range of temperature in the cavity 102 to which the medicine 10 is exposed. In one embodiment, the thermal element is a thermoelectric element. The control module 106 may be configured to receive a temperature reading from the temperature sensor and correlate the temperature with a predetermined temperature threshold based on the tolerances of the medicine 10. The control module 106 may be configured to alert a user if the temperature threshold is crossed and/or cool the cavity 102 via the thermal element. Notifying the user that the temperature threshold has been crossed may include visual indicia such as a message of the display screen 116 or the status indicator module 114, an audible warning alert through the audio-out module 126, a text message or voice message initiated by the contingent aid device 100, or combinations thereof.

The medicine status sensor 110 may include any suitable sensor for measuring whether the medicine 10 is disposed within the cavity 102 or not. Suitable sensors include, but are not limited to, a magnetic sensor, a magnetic contact sensor, a mechanical sensor, an electric circuit sensor, an optical sensor, or combinations thereof.

In one embodiment, the cavity 102 is configured to hold the medicine 10 without altering the medicine 10 or a delivery mechanism of the medicine 10 as received from a manufacturer, a distributor, a pharmacy, a doctor, or a store.

The lid 104 may be connected to the remaining portion of the contingent aid device 100 by any suitable mechanism, including, but not limited to, a mechanical hinge, a living hinge, a snap-fit joint, a threaded joint, or combinations thereof. The lid status sensor 108 may include any suitable sensor for measuring whether the lid 104 is closed or open. Suitable sensors include, but are not limited to, a magnetic sensor, a magnetic contact sensor, a mechanical sensor, an electric circuit sensor, an optical sensor, or combinations thereof.

The control module 106 may include a computer processor and memory associated therewith.

The user-activatable tactile input 112 may be any suitable input device, including, but not limited to, a button, a capacitive button, a toggle, a rocker, a switch, a pointing stick, a joystick, a control pad, a directional pad, a touch pad (also known as a track pad), a scroll wheel, a click-wheel, or combinations thereof. The user-activatable tactile input 112 may specifically include a plurality of different individual inputs which are the same or different (e.g., three buttons and a switch, or one toggle and a control pad, or one click wheel and four buttons, or three capacitive buttons, or any other suitable combinations). In one embodiment, the user-activatable tactile input 112 may be mapped to different interface interactions correlating to the function of the contingent aid device 100 being engaged with. By way of example, where there are three buttons as the user-activatable tactile input 112, each button may have a particular function when the lid 104 is closed, and another function when the lid 104 is open. The mapping of functions to the user-activatable tactile input 112 may reside in the remote server 134 or the control module 106.

Figure 10A:
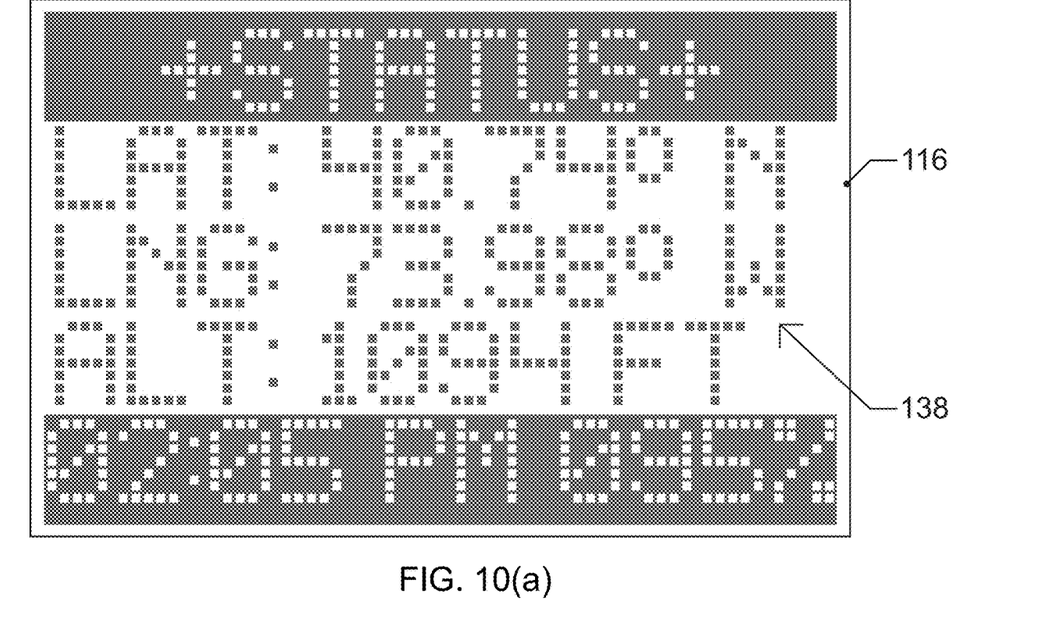
Figure 10B:
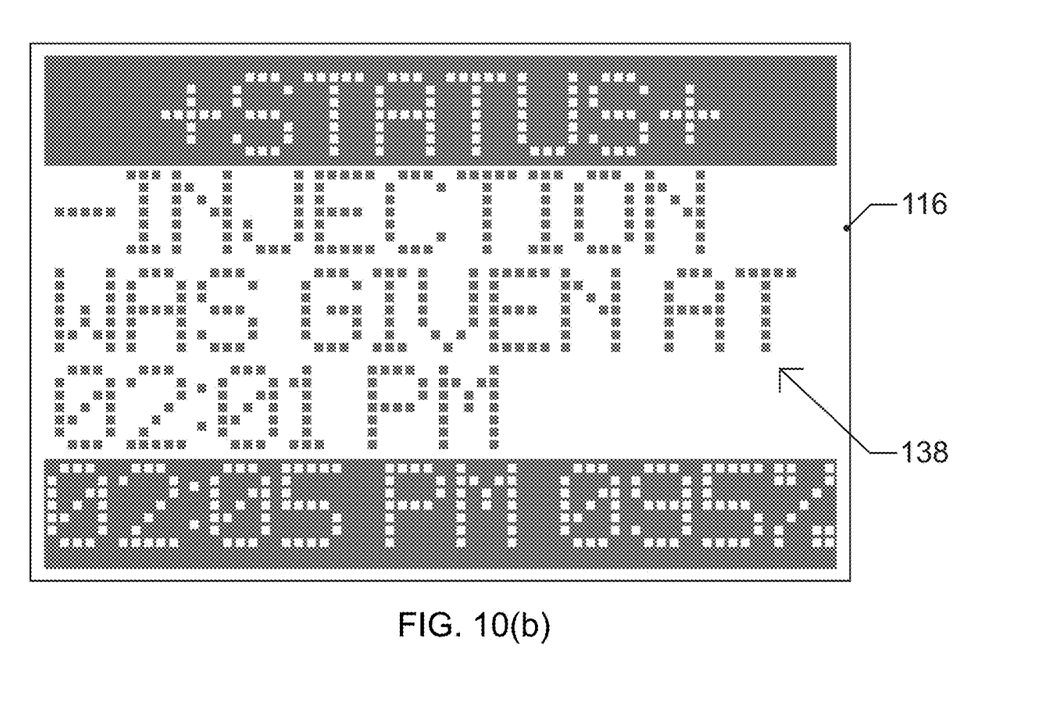

The display screen 116 and the status indicator module 114 may be discrete and distinct elements or the status indicator module 114 may be a virtual module displayed on the display screen 116, or the display screen 116 may be a portion of the status indicator module 114. The display screen 116 may be an LCD screen, an LED screen, a micro-LED screen, a QLED screen, an OLED screen, a touch screen, an electronic paper screen, an interferometric modular display screen, or combinations thereof. In one embodiment, where the display screen 116 and the status indicator module 114 are discrete and distinct elements, the status indicator module 114 may be an additional display screen or one or more discrete lights. If the status indicator module 114 is an additional display screen, the status indicator module 114 may be an LCD screen, an LED screen, a micro-LED screen, a QLED screen, an OLED screen, a touch screen, an electronic paper screen, an interferometric modular display screen, or combinations thereof. If the status indicator module 114 is one or more discrete lights, the one or more discrete lights may be light emitting diodes. FIGS. 10(*a*) and 10(*b*) disclose exemplary contingent aid device 100 status messages for display by a display screen 116 of contingent aid device 100.

The communications module 118 may include a 2G cellular module, a 3G cellular module, a 4G cellular module, a 5G cellular module, a 6G cellular module, a Bluetooth module, a WIFI module, an NFC module, or combinations thereof. Each individual such module or combinations of such modules may include one or a plurality of antennae. The digital-in module 128 may be part of the communication module 118 or separate from the communication module 118. In one embodiment, the digital-in module 128 includes a wired connector such as, but not limited to, a USB connector (1., 2.0, 3.0, 3.1, 3.2, or newer standards), type-A USB connector, a type-B USB connector, a mini-A USB connector, a mini-B USB connector, a micro-A USB connector, a micro-B USB connector, a USB-C connector, a Lightning connector, a Thunderbolt connector, or combinations thereof. The communication module 118 may include a subscriber identity module ("SIM") card (standard or micro) or a plurality of SIM cards for interfacing with cellular networks across a country, across a region, or worldwide.

The altimeter 122 may be a discrete unit separate from the GPS module 120 or may be a component of the GPS module 120. The GPS module 120 may include any suitable antennae which may be share with or distinct from the one or more antennae of the communications module 118. The GPS module 120 may be assisted (A-GPS or A-GNSS) or unassisted. As used herein "GPS" is synonymous with global navigation satellite systems ("GNSS") and is used inclusively with BEIDOU, GALILEO, GLONASS, QZSS, IRNSS, SBAS, StarFire, WAAS, eGNOS, MSAS, GAGAN, and NAVIC, as well as ground-based augmentations systems such as GRAS, and the joint U.S. Coast Guard, Canadian Coast Guard, U.S. Army Corps of Engineers and U.S. Department of Transportation National Differential GPS ("DGPS") service.

The voice-in module 124 may be any suitable microphone, and the audio-out module 126 may be any suitable speaker.

The power source 130 may be any suitable system including, but not limited to, a battery, a rechargeable battery, a permanent battery, a removable battery, or combinations thereof.

The contingent aid device 100 may further include an accelerometer 132, wherein the control module 106 is configured to deactivate the GPS module 120 after a third predetermined period in which the contingent aid device 100 is at rest and reactivate the GPS module 120 following movement of the contingent aid device 100. The third predetermined period may be any suitable period including, but not limited to, 5 minutes, 10 minutes, 15 minutes, 30 minutes, 45 minutes, 1 hour, 2 hours, 5 hours, 12 hours, 1 day, 2 days, 5 days, 1 week. Deactivating and reactivating the GPS module 120 may increase the battery life of the contingent aid device 100 by conserving power. During periods of time in which the GPS module 120 is deactivated due to lack of movement, the contingent aid device 100, the at least one remote server 134 (FIG. 6), or both, may store the most recent GPS locational information for use until the GPS module 120 is reactivated following movement. In a further embodiment, in addition to the GPS module 120 being reactivated following movement of the contingent aid device 100 as determined by the accelerometer 132, the GPS module 120 may also be reactivated by the lid 104 of the contingent aid device 100 being opened or a user engaging the user-activatable tactile input 112.

The first predetermined period of time after opening of the lid 104 without removal of the medicine 10 from the cavity 102 may be any suitable period of time, including, but not limited to, 15 seconds, alternatively 30 seconds, alternatively 45 second, alternatively 1 minute, alternatively 2 minutes, alternatively at least 3 minutes. The second predetermined period of time may be any suitable period of time, including, but not limited to, 15 seconds, alternatively 30 seconds, alternatively 45 second, alternatively 1 minute, alternatively 2 minutes, alternatively at least 3 minutes.

The contingent aid device 100 may further include one or more additional cavities configured to hold at least one additional medicine in addition to the cavity 102 which is configured to hold the medicine 10. The one or more additional cavities may have the same geometry as the cavity 102 or distinct geometries from the cavity 102. The one or more additional cavities may have the same geometry as the cavity 102 when the cavity 102 and the one or more additional cavities are configured to hold the same medicine 10, or different medicines which are disposed in medicine containers 12 having the same form factors (such as, by way of example, the same form factor pill vials), or where the contingent aid device 100 is used with medicine-specific inserts where the inserts are externally adapted to fit the same size cavity 102 and are internally adapted to contain medicine containers 12 having different form factors, by way of example where the inserts are constructed or molded for specific medicine container 12 form factors or where the inserts include shock-absorbing padding which conforms to different form factor medicine containers 12.

The medicine 10 may be any suitable composition, including, but not limited to, an emergency use medication, albuterol, ammonia, antihistamine, aspirin, atropine, diphenhydramine, ephedrine, epinephrine, flumazenil, glucagon, hydrocortisone, lorazepam, midazolam, morphine, naloxone, nitroglycerine, salbutamol, or combinations thereof. The medicine 10 may be disposed in a medicine container 12 selected from the group consisting of a vial, an inhaler, an auto-injector 14, a syringe, a nasal spray, an ampule, a packet, a wrapper, a pouch, or combinations thereof. The medicine 10 itself may be in any appropriate form as disposed within the medicine container 12, including, but not limited to, pills, liquids, vapors, comestible films, or combinations thereof.

In one embodiment, the contingent aid device 100 is configured to initiate communication with a PSAP as the emergency contact. Although PSAP typically specifically refers to a government-run public-safety answering point, as used herein "PSAP" is more expansive, covering not just government-run public-safety answering points as used in the United States of America, but also functional equivalents which may be referred to with different names in other countries as well as private emergency answering points which are used to supplant or supplement government-run PSAPs (e.g., ECC in Canada, and private operators such as Intrando and Vesta, and Bandwidth). The contingent aid device 100 may be further configured to initiate communication with a personal emergency contact pre-configured by a user, such as a parent, spouse, partner, child, friend or other person of personal significance.

In another embodiment, the contingent aid device 100 is configured to initiate communication with a non-PSAP individual or entity as the emergency contact, such as, but not limited to, a friend, a family member, a colleague, a first responder network such as, but not limited to, FirstNet, an ambulance dispatch or company, or non-PSAP emergency service provider. The non-PSAP individual or entity may be fully predetermined (only one programmed), predetermined with options (selected from a pre-programmed list), or determined at the time of activation of the contingent aid device 100. In a further embodiment, the contingent aid device 100 is configured to offer a user an option of contacting the PSAP as the emergency contact, the non-PSAP individual or entity as the emergency contact, or both the PSAP and the non-PSAP individual or entity as the emergency contact (with either the PSAP or the non-PSAP individual or entity being contacted first and the other second, or with the PSAP and the non-PSAP individual or entity being contacted simultaneously simultaneously). Considerations for choosing between a PSAP or a non-PSAP individual or entity may include, but are not limited to, a user's familiarity with his or her own health needs, the symptoms being experiences by a user, costs likely to be incurred as a result of the decision, pre-existing service agreements or other contractual relationships, or combinations thereof.

Initiating communication with an emergency contact may include transmitting (direct) or initiating transmission (indirect) of a voice message to the emergency contact. The primary difference between the direct and indirect transmission method is that in the direct method, the voice message is created and/or stored on the contingent aid device 100 itself, whereas in the indirect transmission method, the voice messages are created and/or stored on at least one remote server 134 in electronic communication with the contingent aid device 100.

In one embodiment, the contingent aid device 100 or the remote server 134 generates an artificial voice message via text-to-voice or similar technology as the voice message. The contingent aid device 100 or the remote server 134 may iterate location coordinates of the contingent aid device 100 during the artificial voice message with increasing accuracy over the duration of the artificial voice message as the GPS module 120 resolves the location coordinates.

In another embodiment, the contingent aid device 100 or the remote server 134 transmits a pre-recorded voice message as the voice message. The contingent aid device 100 or the remote server 134 may cut artificial voice iterations of location coordinates of the contingent aid device 100 into the pre-recorded voice message via text-to-voice with increasing accuracy over the duration of the pre-recorded voice message as the GPS module 120 resolves the location coordinates.

It is noted that because the contingent aid device 100 is configured to, without further user-initiated instruction or action, initiate communication with an emergency contact following user activation of the user-activatable tactile input 112, the contingent aid device 100 offers a secondary usage beyond seeking assistance related to the condition for which the medicine 10 is intended. A user may use the contingent aid device 100 seeking assistance from an emergency contact for a medical emergency unrelated to the condition treated by the medicine (e.g., a contingent aid device 100 with medicine for treating an allergic reaction may also be used to summon aid for a heart attack), or the contingent aid device 100 may be used to seek assistance for a non-medical situation such as a criminal matter (e.g., a domestic violence situation, a robbery, or a kidnapping).

Figure 1:
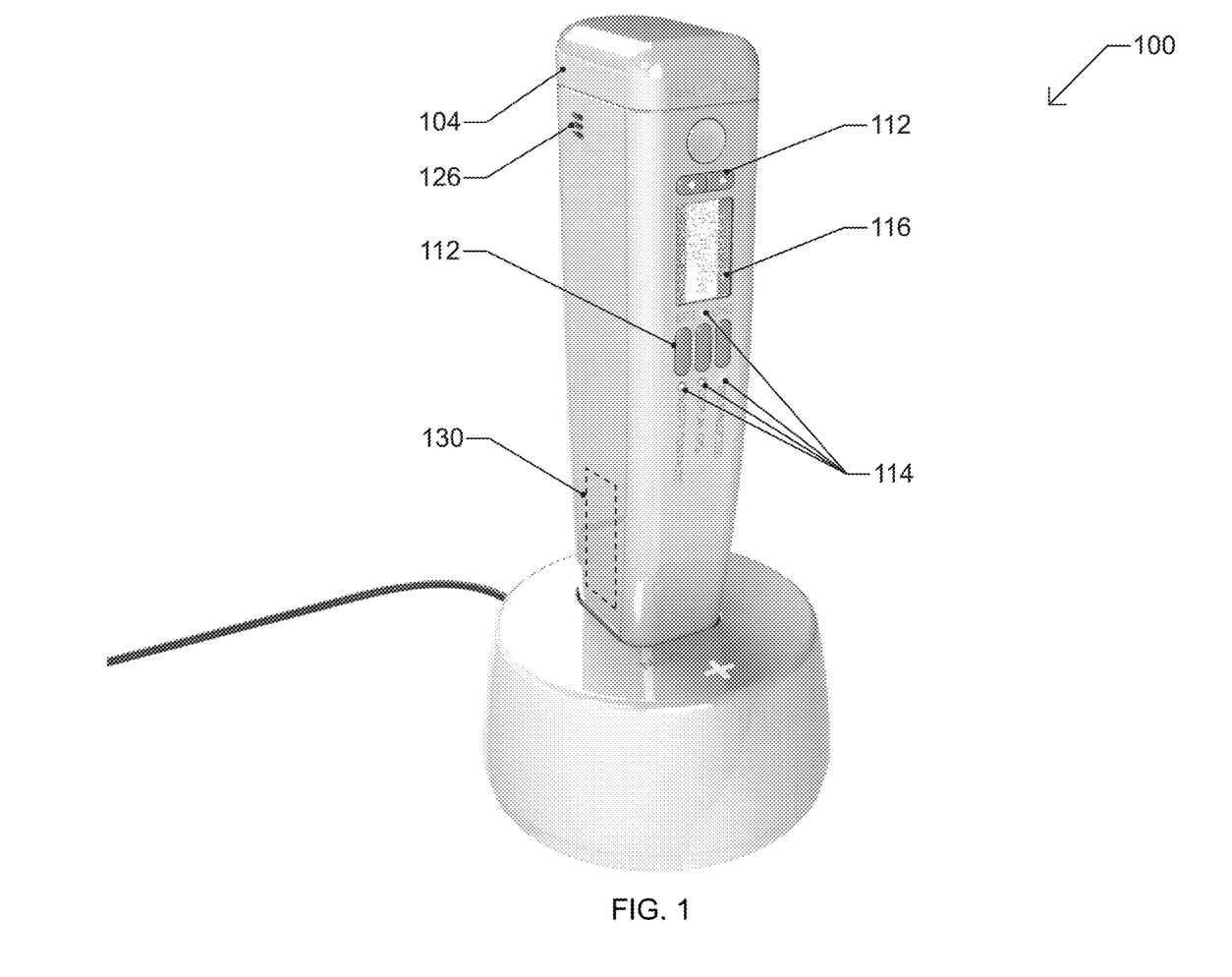
FIG. 1 is a perspective view of a contingent aid device with lid closed and disposed in a charging station, according to an embodiment of the present disclosure.
Figure 2:
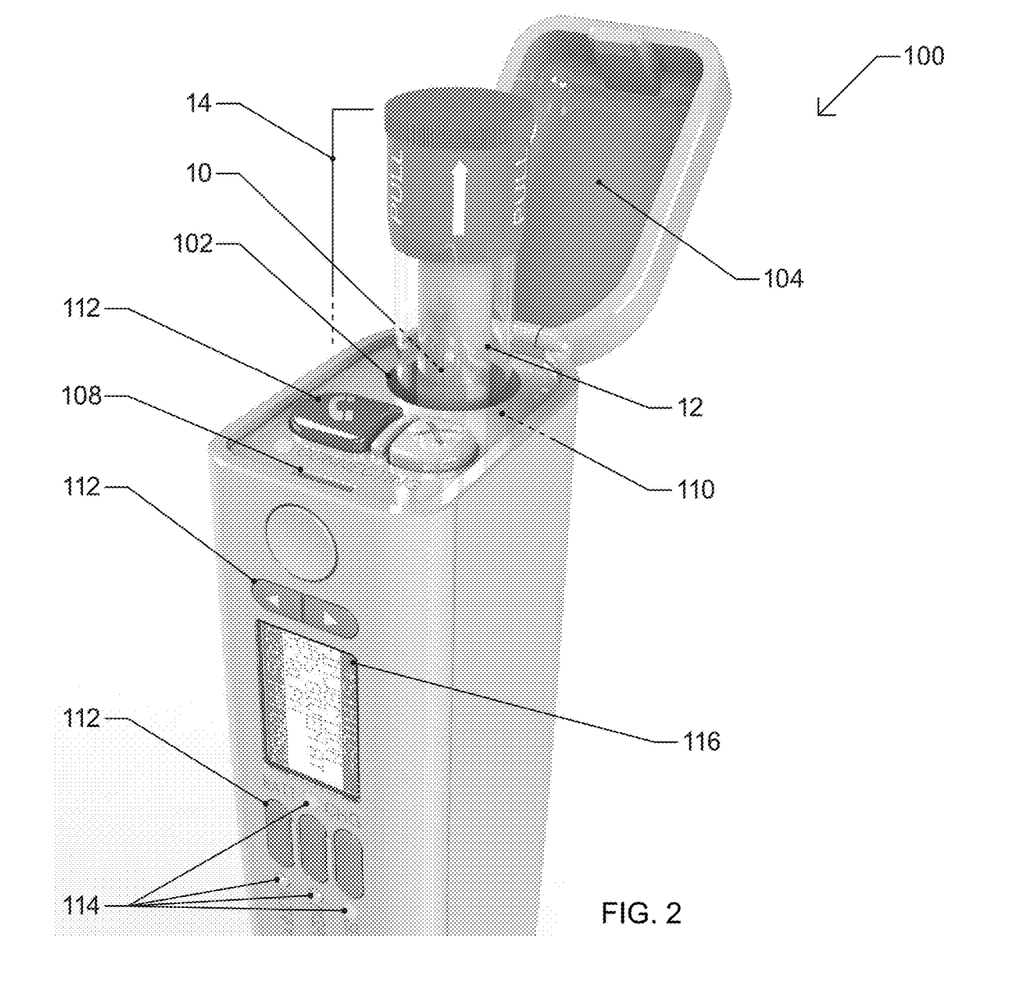
FIG. 2 is a perspective view of the contingent aid device of FIG. 1 with the lid open and the medicine disposed in the cavity but partially exposed, according to embodiments of the present disclosure.
Figure 3:
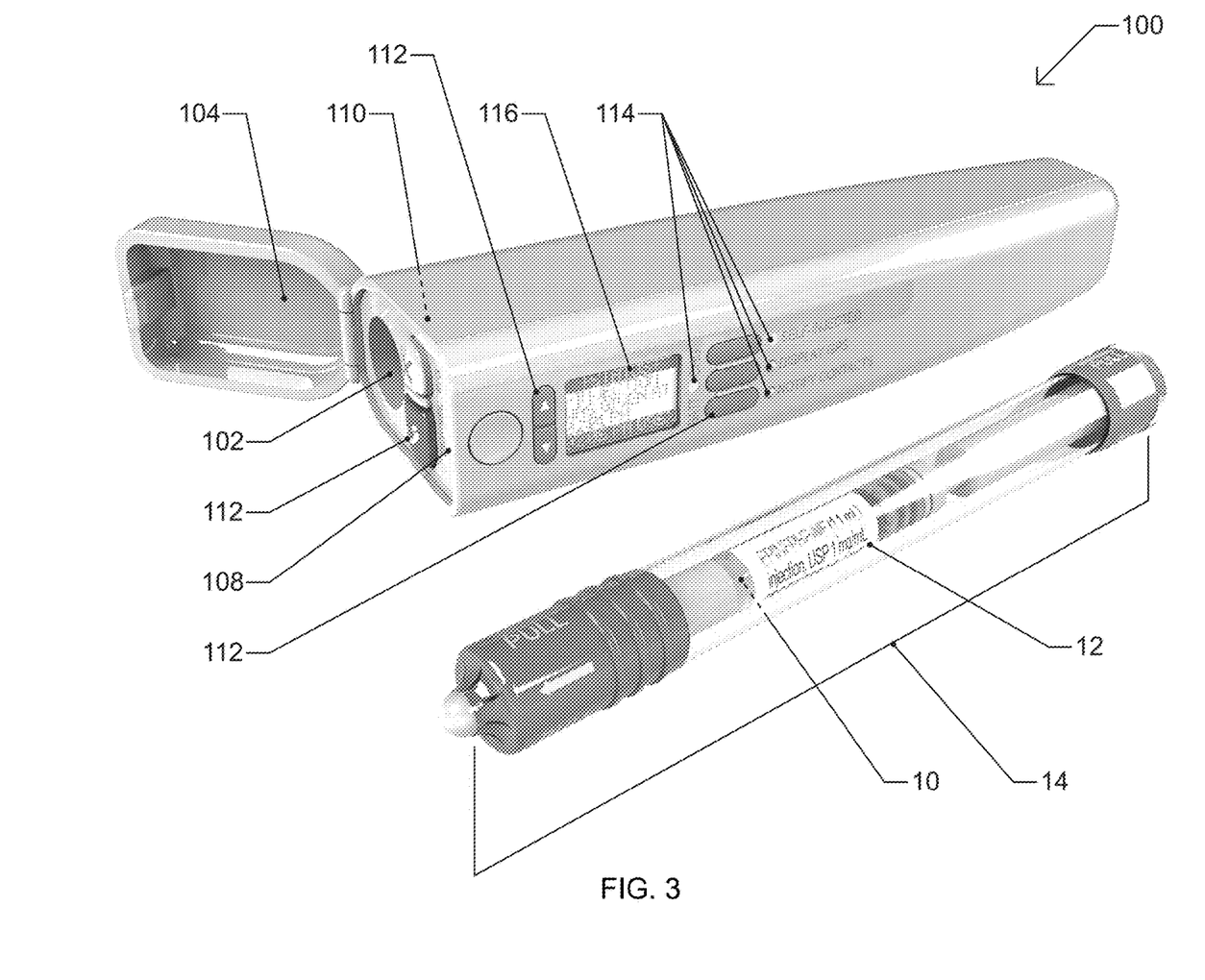
FIG. 3 is a perspective view of the contingent aid device of FIG. 1 with the lid open and the medicine removed from the cavity, according to embodiments of the present disclosure.
Figure 4:
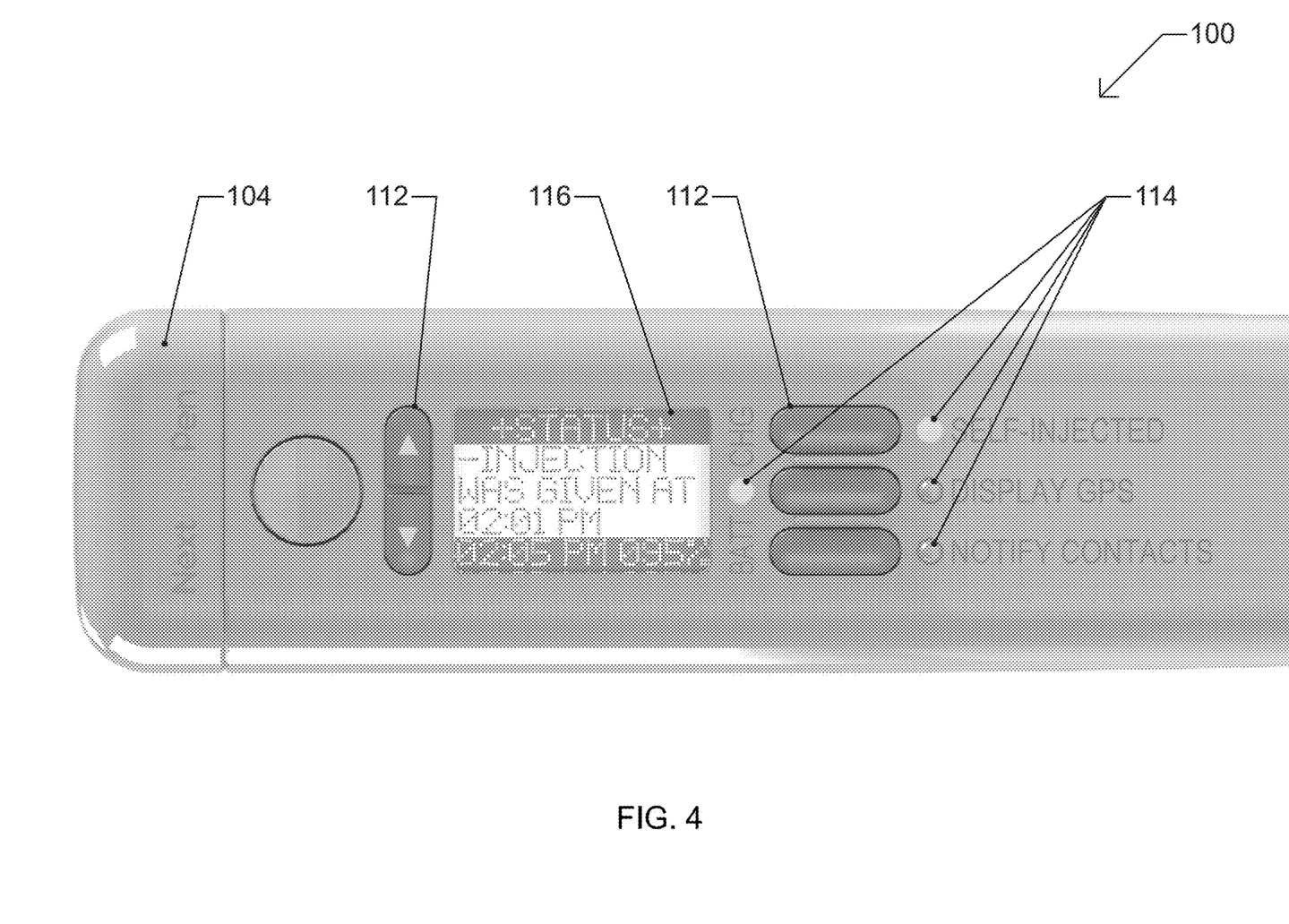
FIG. 4 is a front view of the contingent aid device of FIG. 1 with the lid closed, according to embodiments of the present disclosure.
Figure 5:
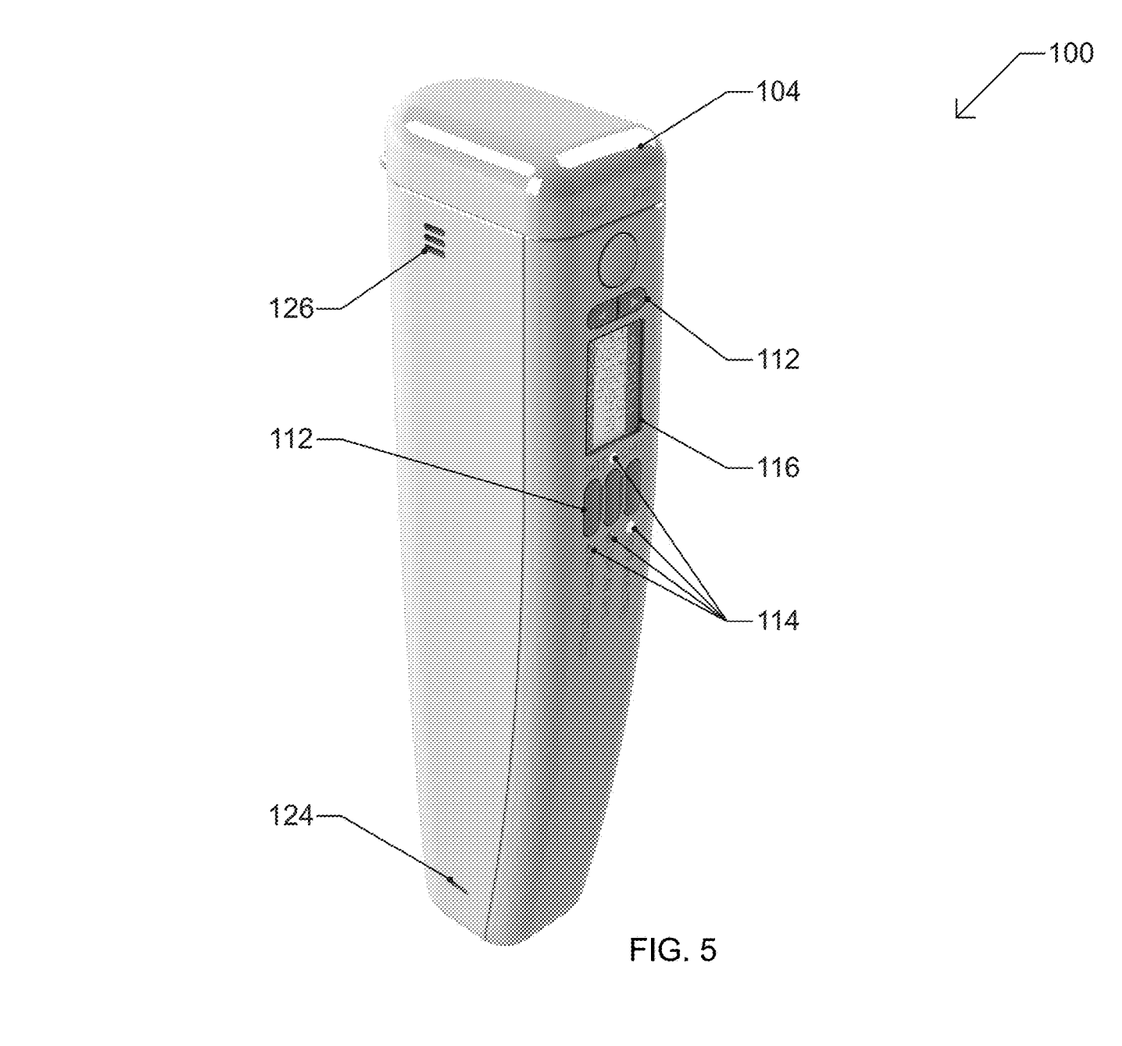
FIG. 5 is a side view of the contingent aid device of FIG. 1 with the lid closed, according to embodiments of the present disclosure.
Figure 6:
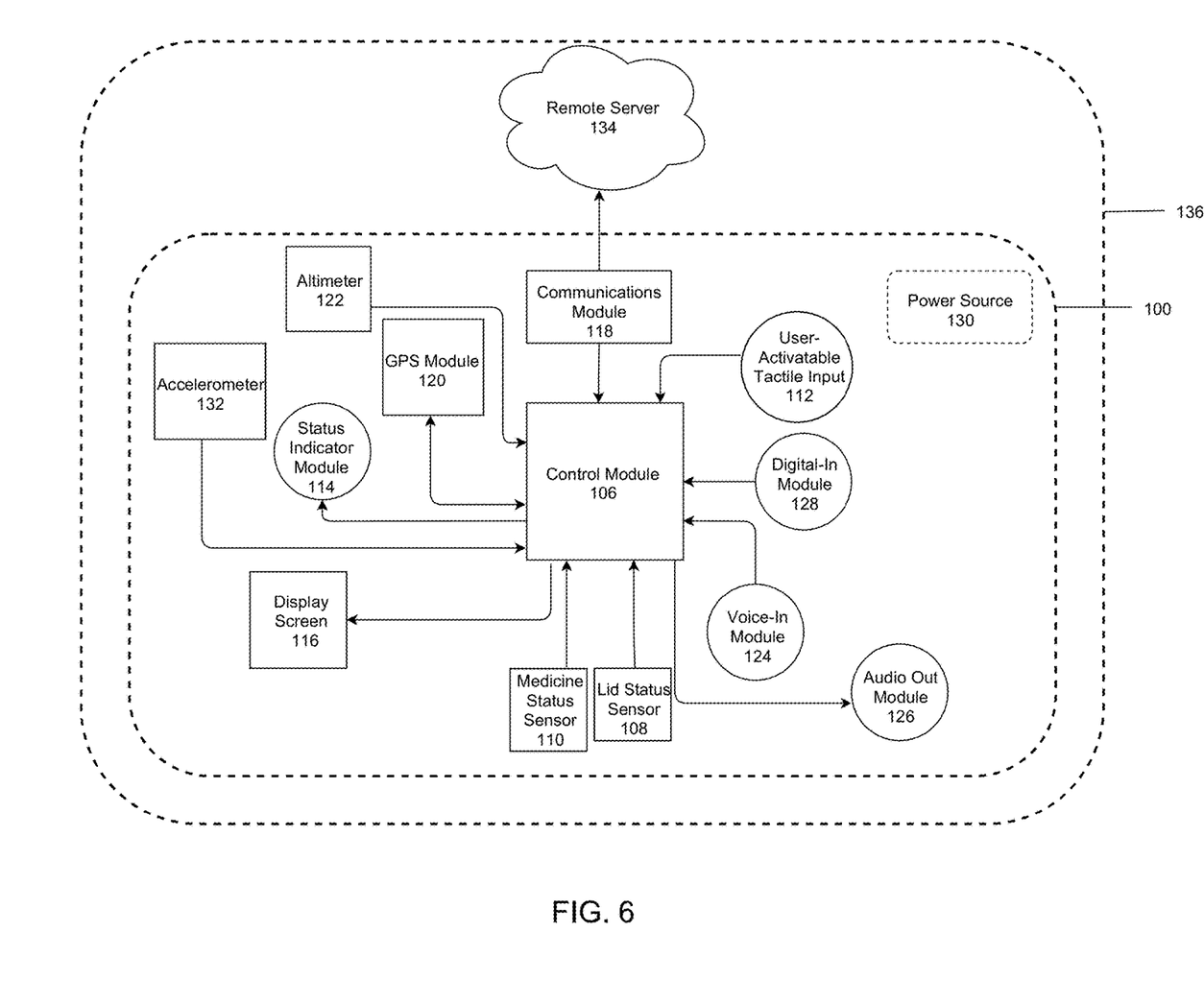
FIG. 6 is a schematic representation of a system for contingent aid communication, according to an embodiment of the present disclosure.
Figure 9:
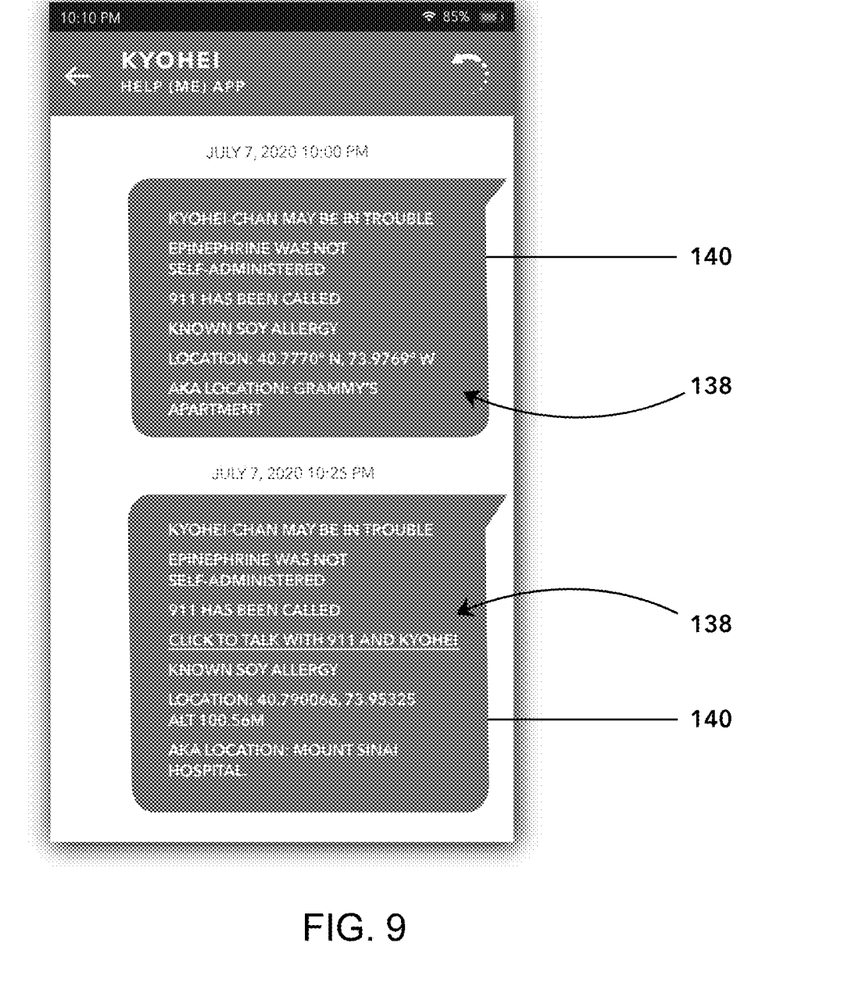
FIG. 9 is a sample app screen or texts received by a person of personal significance following activation of a contingent aid device, according to an embodiment of the present disclosure.

Referring to FIG. 6, in one embodiment, a system 136 for contingent aid communication includes the contingent aid device 100 and at least one remote server 134 in electronic communication with the control module 106 through the communication module 118. The remote server 134 may be configured to communicate with the emergency contact by transmitting, when the PSAP is configured to receive user information 138 over internet protocol (IP), data to the PSAP over IP including a message requesting assistance, locational data of the contingent aid device 100 with longitude, latitude, and elevation, as well as an address when available, and, optionally, information regarding an emergency for which the medicine containing 12 storing the medicine 10 is removed from the cavity 102. When the PSAP is not configured to receive the user data 138 over IP, the remote server 134 may be configured to transmit a voice message to the PSAP including the request for assistance, the locational data of the contingent aid device 100 with the longitude, the latitude, and the elevation, as well as the address when available, and, optionally, the information regarding the emergency for which the medicine container 12 storing the medicine 10 is removed from the cavity 102. The data over IP or the voice message may include additional user information 138 such as a visual description of the user and a list of all actions which the contingent aid device 100 has a record of having taken place or not (e.g., whether or not the medicine 10 disposed in the medicine container 12 has been used). The remote server 134 may further be configured to transmit text messages to a predetermined recipient list with status updates including user actions taken or not taken with the contingent aid device following an initial user activated trigger, as well as the updated location of the use (FIG. 9 shows a sample app screen or texts received by a person of personal significance following activation of a contingent aid device 100). As used herein, "text messages" are inclusive of SMS text messages and MMS text messages, and may therefore include embedded digital images, videos, sound files, emoji, or combinations thereof.

By way of example, a recorded to text-to-speech-generated voice message for an exemplary user named "Kyohei" may include a script such as:

My name is Kyohei, I am 10 years old. My location is (civic location) (followed by (latitude coordinate value, longitude coordinate value, altitude value). I need an ambulance. I am severely allergic to peanuts and I am having a reaction and can go into anaphylaxis at any time now. My device called you because I cannot talk right now. Please send help. Again, my name is Kyohei . . . I am 10 . . . my location is (civic address, followed by latitude, longitude, altitude (z), range of error). I need an ambulance now. My emergency contact cell phone number is (XXX-XXX-XXXX), and my parent might be available to talk to you if you call that number.

In a further embodiment of the system 136 for contingent aid communication, the remote server 134 is further configured to establish at least one of a text message communication pathway or a voice party line between a user of the contingent aid device 100, at least one member of the predetermined recipient list, and the PSAP by which the at least one member may communicate with the PSAP. Via this party line, by way of example, a parent may be able to notify the PSAP of a child's underlying conditions even if the parent is not present with the child who used the contingent aid device 100, and the child may be comforted by the parent's voice even if the child is unable to speak. The party line may be established by sending a text or call meta data with an embedded link to access the party line to the PSAP and at least one member of the predetermined recipient list.

In one embodiment of the system 136 for contingent aid communication, the contingent aid device 100 is configured such that in the event that the voice message is unable to be sent by the remote server 134 or received by the nearest PSAP, or the contingent aid device 100 is disconnected from communication with the remote server 134, the contingent aid device 100 places a standard cellular emergency call.

In one embodiment, a contingent aid communication method includes, upon an initial user activated trigger, without further user-initiated instruction or action, the contingent aid device 100 initiates communication with an emergency contact. Initial user activated triggers include, but are not limited to, removing medicine 10 from a contingent aid device 100, user activation of a user-activatable tactile input 112 of the contingent aid device 100, passing of a first predetermined period of time after opening the contingent aid device 100 without removal of the medicine 10 from the contingent aid device 100, or passing of a second predetermined period of time after removal of the medicine 10 from the contingent aid device 100 without user activation of the user-activatable tactile input 112 confirming the medicine 10 has been administered. The communication with the emergency contact may include, but is not limited to, directing the remote server 134 to transmit a voice message to a nearest PSAP including a request for assistance and user information 138 such as locational data of the contingent aid device 100 with longitude, latitude, and elevation, as well as an address when available, and, optionally, information regarding an emergency for which the medicine 10 is released, transmitting text messages to a predetermined recipient list with status updates including user actions taken or not taken with the contingent aid device 100 following the initial user activated trigger, in the event that the voice message is unable to be sent by the remote server 134 or received by the nearest PSAP, initiating communication with an emergency contact by placing a standard cellular emergency call. The status updates texted transmitted may include embedded links or access information for joining a party line (as shown in FIG. 9).

Figure 7:
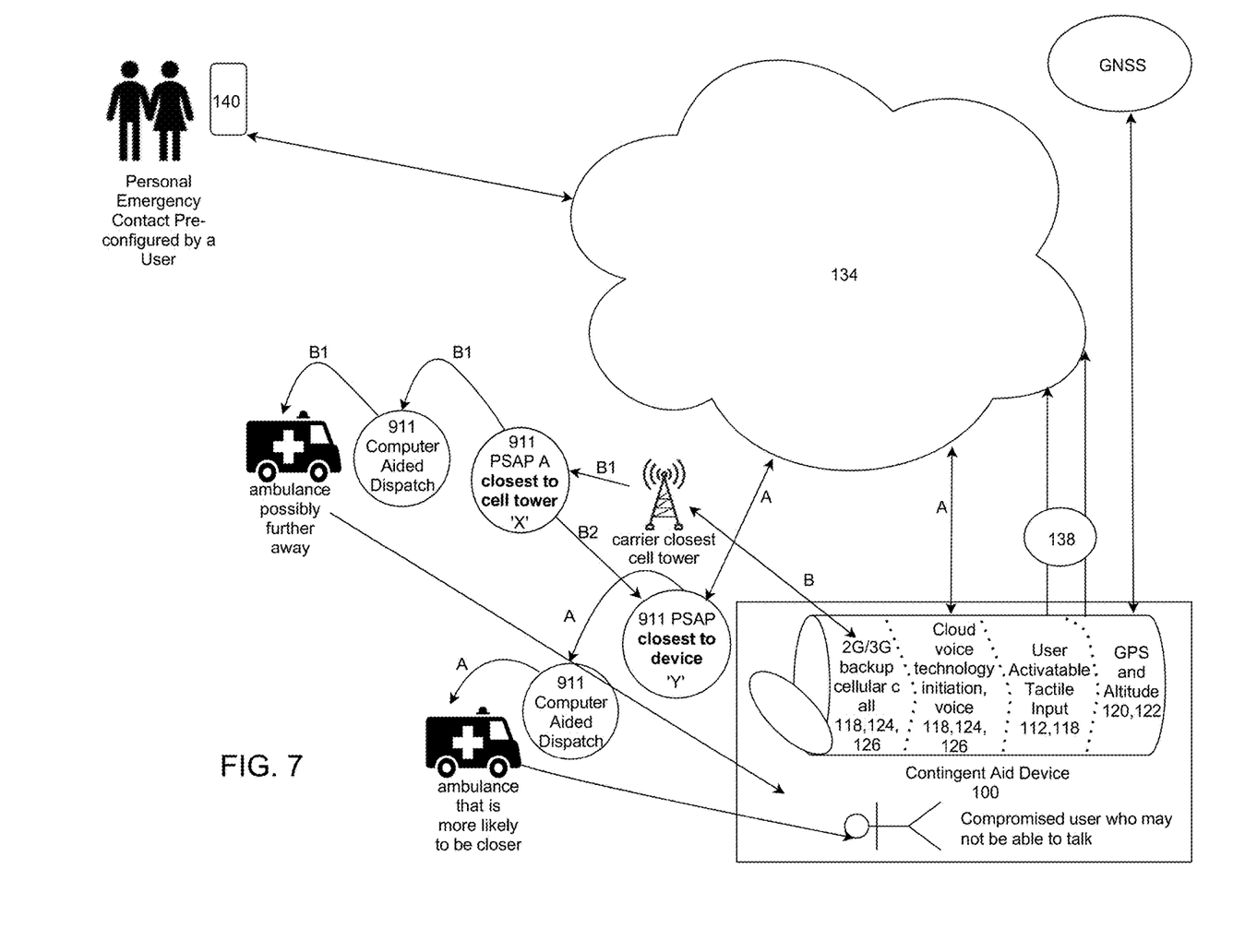
FIG. 7 is a schematic representation of a communication pathway for a system for contingent aid communication, according to an embodiment of the present disclosure.

Referring to FIG. 7, in one exemplary embodiment, a communication path A for the system 136 for contingent aid communication is from a contingent aid device 100 to at least one remote server 134 using mixed voice technologies (pre-recorded voice, GPS coordinates with altitude, text-to-voice, and, optionally, live audio communication) to transmit all required user information 138 to a PSAP. This communication path may be routed directly to the PSAP from the remote server 134 without passing through an intermediate manned call center (although in certain embodiments, the communication path may be routed through an intermediate manned call center prior to reaching the PSAP). When the PSAP closest to the contingent aid device 100 answers, the message formed by the mixed voice technologies plays, giving an operator at the PSAP the user information 138 needed to dispatch an ambulance. If, however, there is an issue with the communication path A, a redundant path B is engaged with a traditional call emergency pathway via 2G or 3G cellular. This communication may not go to the nearest PSAP to the user, and the user may have to answer multiple questions from the PSAP operator at one or more PSAP before an ambulance is dispatched to the user. If a user is unable to speak, the PSAP operator may be unable to learn the precise location at which aid is needed unless a bystander is able to assist. In a further embodiment, in redundant path B and provided that the user is compromised, the contingent aid device 100 may use talk-to-text to vocalize the location of the contingent aid device 100 as well as indicating that the user is unable to communicate and any other available user information 138.

Figure 8:
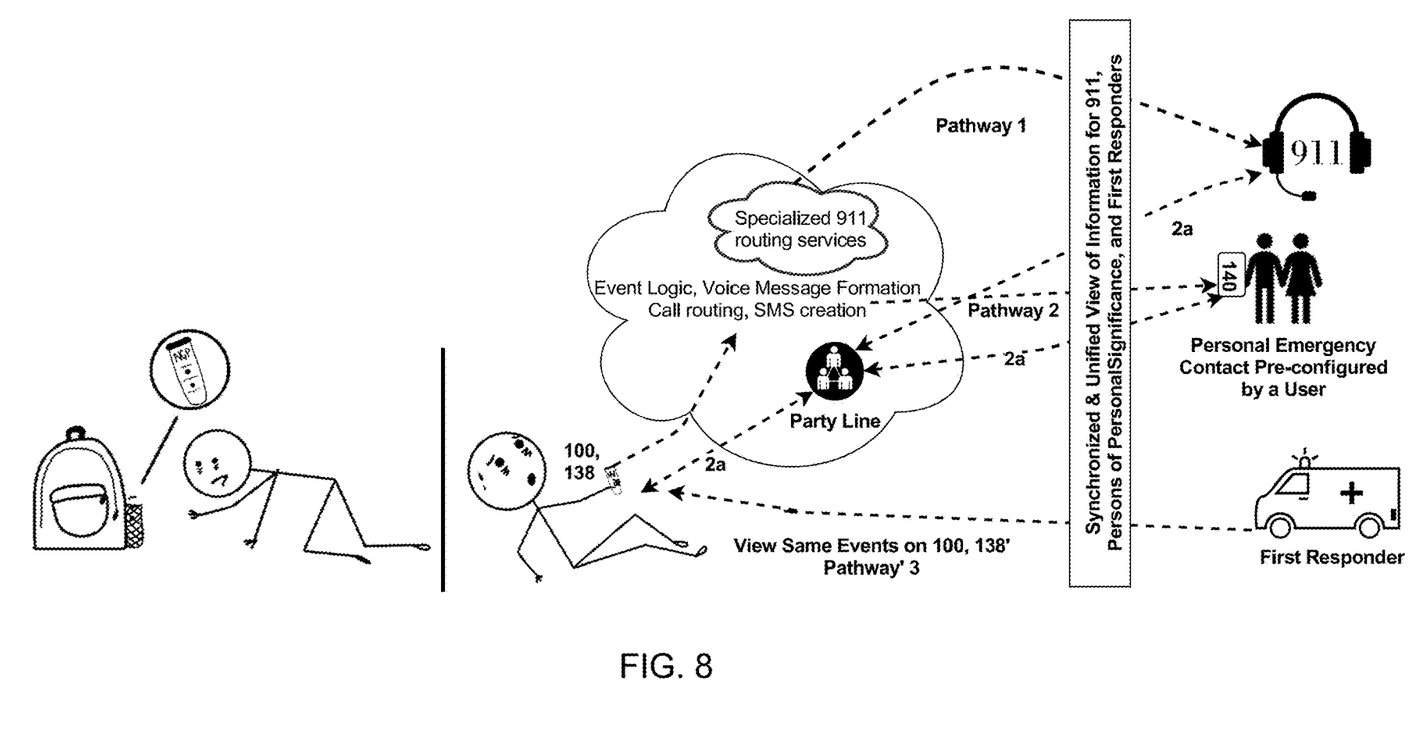
FIG. 8 is a schematic representation of a synchronized and unified view of information for an emergency contact, persons of personal significance, and first responders, according to an embodiment of the present disclosure.

Referring to FIG. 8 in respect to communication path A as shown in FIG. 7, this communication path A provides synchronized and unified information views for PSAPs, persons of personal significant to the user, and first responders. User events 140 containing user information 138 are sent (paths 1 and 2a) via the remote server 134 using APIs to PSAPs able to except them, particularly where the PSAPs are unable to accept SMS text or NextGeneration 911 information. These same user events 140 are also streamed (paths 2 and 2a) to pre-configured persons of significance (FIG. 9). A holder of the contingent aid device 100, who may be the compromised device user, a bystander, or a first responder, is also presented (path 3) the same user information 138 (FIG. 7) on the display screen 116 of the contingent aid device 100 (FIG. 10).

While a user may have a choice to contact a PSAP or a non-PSAP person or entity as the emergency contact through the contingent aid device 100, in the event that a user does not select between the PSAP or the non-PSAP person or entity, the contingent aid device 100 may default to initiating contact with the PSAP. In one embodiment, when the contingent aid device 100 is activated, the remote server 134 logs time-stamped user events 140 generated from device-side tactile user inputs along with associated GPS coordinating, including the elevation coordinate.

If the user chooses to notify a non-PSAP person or entity (e.g., a person of personal significance to the user), for a period of about 1-3 hours depending on battery life and system resource optimization, the contingent aid device 100 and the remote server 134 cooperate to stream user events 140 to the non-PSAP person or entity. If the user chooses to notify the non-PSAP person or entity, but does not take further action after opening the lid 104 (such as removing the medicine container 12 holding the medicine 10 from the cavity 102 or indicating through the user-activatable tactile input 112 that the medicine 10 was taken), the remote server 134 may contact a PSAP for assistance. If the user opens the lid 104 and takes the medicine 10, but later becomes unable to talk the user's persons of personal significance may still be notified of the user's condition and location through the user events 140 which are promulgated by the remote server 134.

If, however, the user tactile input indicates to call for emergency services (through a PSAP), a call is routed from the remote server 134 (optionally though a propriety third part call routing service, such as, but not limited to, Bandwith or Intrado) to the PSAP closest to the contingent aid device 100. The user has an option to hang-up or cancel the call to the PSAP through the user-activatable tactile input 112.

Regardless of which option the user chooses, if the remote server 134 is unable to route the call as intended, the remote server may default to a 2G/3G standard cellular call, and if the contingent aid device 100 is unable to contact the remote server 134, then the contingent aid device 100 may default to a 2G/3G standard cellular call.

The at least one remote service 134 may include a private server, a Twilio server, a Bandwidth server, an Intrado server, an ESINET server, a FirstNet server, or combinations thereof.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A contingent aid device, comprising:
   a cavity configured to hold a medicine;
   a lid configured to retain the medicine in the cavity when closed and render accessible the medicine when open;
   a control module;
   a lid status sensor configured to signal the control module if the lid is opened;
   a medicine status sensor configured to signal the control module if the medicine is removed from the cavity;
   a user-activatable tactile input;
   a status indicator module;
   a display screen;
   a communication module;
   a global positioning system (GPS) module;
   an altimeter;
   a voice-in module;
   an audio-out module;
   a digital-in module; and
   a power source,
   wherein the contingent aid device is configured to, without further user-initiated instruction or action, initiate communication with an emergency contact including a public-safety answering point (PSAP) following:
   removal of the medicine from the cavity;
   user activation of the user-activatable tactile input;
   a first predetermined period of time after opening of the lid without removal of the medicine from the cavity; or
   a second predetermined period of time after removal of the medicine from the cavity without user activation of the user-activatable tactile input confirming the medicine has been administered, and
   wherein the communication includes a message requesting assistance, an indication of whether or not the medicine has been removed from the cavity, locational data of the contingent aid device, and information regarding an emergency for which the medicine is removed from the cavity.

2. The contingent aid device of claim 1, further including at least one additional cavity configured to hold at least one additional medicine.

3. The contingent aid device of claim 2, wherein the cavity and the at least one additional cavity have different geometries so as to hold medicine containers having different form factors.

4. The contingent aid device of claim 1, wherein the cavity is configured to hold the medicine without altering the medicine or a delivery mechanism of the medicine as received from a manufacturer, a distributor, a pharmacy, a doctor, or a store.

5. The contingent aid device of claim 1, wherein the contingent aid device is configured to initiate communication with both a non-PSAP individual or entity and the PSAP as the emergency contact.

6. The contingent aid device of claim 5, wherein the contingent aid device is further configured to initiate communication with a personal emergency contact pre-configured by a user.

7. The contingent aid device of claim 1, wherein the medicine is selected from the group consisting of albuterol, ammonia, antihistamine, aspirin, atropine, diphenhydramine, ephedrine, epinephrine, flumazenil, glucagon, hydrocortisone, lorazepam, midazolam, morphine, naloxone, nitroglycerine, salbutamol, and combinations thereof.

8. The contingent aid device of claim 1, wherein the medicine is disposed in a medicine container selected from the group consisting of a vial, an inhaler, an auto-injector, a syringe, a nasal spray, an ampule, a packet, a wrapper, a pouch, and combinations thereof.

9. The contingent aid device of claim 1, wherein the contingent aid device is configured to transmit or initiate transmission of a voice message to the emergency contact.

10. The contingent aid device of claim 9, wherein the contingent aid device or a remote server generates an artificial voice message via text-to-voice as the voice message.

11. The contingent aid device of claim 10, wherein the contingent aid device or the remote server iterates location coordinates of the contingent aid device during the artificial voice message with increasing accuracy over a duration of the of the artificial voice message as the GPS module resolves the location coordinates.

12. The contingent aid device of claim 9, wherein the contingent aid device or a remote server transmits a pre-recorded voice message as the voice message.

13. The contingent aid device of claim 12, wherein the contingent aid device or the remote server cuts artificial voice iterations of location coordinates of the contingent aid device into the pre-recorded voice message via text-to-voice with increasing accuracy over a duration of the pre-recorded voice message as the GPS module resolves the location coordinates.

14. The contingent aid device of claim 1, further including an accelerometer, wherein the control module is configured to deactivate the GPS module after a third predetermined period in which the contingent aid device is at rest and reactivate the GPS module following movement of the contingent aid device.

15. A system for contingent aid communication, comprising:
   a contingent aid device, including:
   a cavity configured to hold a medicine;
   a lid configured to retain the medicine in the cavity when close and render accessible the medicine when open;
   a control module;
   a lid status sensor configured to signal the control module if the lid is opened;
   a medicine status sensor configured to signal the control module if the medicine is removed from the cavity;
   a user-activatable tactile input;
   a status indicator module;
   a display screen;
   a communication module;
   a global positioning system (GPS) module;
   an altimeter;
   a voice-in module;
   an audio-out module;
   a digital-in module; and
   a power source; and
   a remote server in electronic communication with the control module through the communication module,
   wherein the contingent aid device is configured to, without further user-initiated instruction or action, initiate communication with an emergency contact including a public-safety answering point (PSAP) following:
   removal of the medicine from the cavity;
   user activation of the user-activatable tactile input;

a first predetermined period of time after opening of the lid without removal of the medicine from the cavity; or a second predetermined period of time after removal of the medicine from the cavity without user activation of the user-activatable tactile input confirming the medicine has been administered, and wherein the communication includes a message requesting assistance, an indication of whether or not the medicine has been removed from the cavity, locational data of the contingent aid device, and information regarding an emergency for which the medicine is removed from the cavity.

16. The system for contingent aid communication of claim 15, wherein the remote server is configured to communicate with a nearest PSAP as the PSAP such that:

when the PSAP is configured to receive data over internet protocol (IP), the remote server is configured to transmit data to the PSAP over IP including the message requesting assistance, the locational data of the contingent aid device with longitude, latitude, and elevation, as well as an address when available, and the information regarding an emergency for which the medicine is removed from the cavity; and when the PSAP is not configured to receive the data over IP, the remote server is configured to transmit a voice message to the PSAP including the message requesting assistance, the locational data of the contingent aid device with the longitude, the latitude, and the elevation, as well as the address when available, and the information regarding the emergency for which the medicine is removed from the cavity.

17. The system for contingent aid communication of claim 16, wherein the remote server is further configured to transmit text messages to a predetermined recipient list with status updates including user actions taken or not taken with the contingent aid device following an initial user activated trigger.

18. The system for contingent aid communication of claim 17, wherein the remote server is further configured to establish at least one of a text message communication pathway or a voice party line between a user of the contingent aid device, at least one member of the predetermined recipient list, and the PSAP for communication of the at least one member with the PSAP.

19. The system for contingent aid communication of claim 16, wherein contingent aid device is configured such that in an event that the voice message is unable to be sent by the remote server or received by the nearest PSAP, or the contingent aid device is disconnected from communication with the remote server, the contingent aid device places a standard cellular emergency call.

20. A contingent aid communication method, comprising:

upon an initial user activated trigger selected from the group consisting of:

removing a medicine from a contingent aid device;

user activation of a user-activatable tactile input of the contingent aid device;

passing of a first predetermined period of time after opening the contingent aid device without removal of the medicine from the contingent aid device; and passing of a second predetermined period of time after removal of the medicine from the contingent aid device without user activation of the user-activatable tactile input confirming the medicine has been administered, without further user-initiated instruction or action, the contingent aid device initiates communication with an emergency contact, communication with the emergency contact including:

directing a remote server to transmit a voice message to a nearest public safety answering point (PSAP) including a request for assistance, locational data of the contingent aid device with longitude, latitude, and elevation, as well as an address when available, and, optionally, information regarding an emergency for which the medicine is released;

transmitting text messages to a predetermined recipient list with status updates including user actions taken or not taken with the contingent aid device following the initial user activated trigger; and in an event that the voice message is unable to be sent by the remote server or received by the nearest PSAP, initiating communication with an emergency contact by placing a standard cellular emergency call, wherein the contingent aid device includes:

a cavity configured to hold the medicine;

a lid configured to retain the medicine in the cavity when closed and render accessible the medicine when open;

a control module;

a lid status sensor configured to signal the control module if the lid is opened;

a medicine status sensor configured to signal the control module if the medicine is removed from the cavity;

a user-activatable tactile input;

a status indicator module;

a display screen;

a communication module;

a global positioning system (GPS) module;

an altimeter;

a voice-in module;

an audio-out module;

a digital-in module; and a power source.

* * * * *